United States Patent
Hoff et al.

(10) Patent No.: US 11,090,422 B2
(45) Date of Patent: Aug. 17, 2021

(54) EQUIPMENT DOCKING INTERFACE WITH LATCH MECHANISM FOR HEART-LUNG MACHINE

(71) Applicant: Maquet Cardiopulmonary GmbH, Rastatt (DE)

(72) Inventors: Robert Hoff, Boonton, NJ (US); Daniel A. Walters, Rockaway Township, NJ (US)

(73) Assignee: MAQUET CARDIOPULMONARY GMBH, Rastatt (DE)

( * ) Notice: Subject to any disclaimer, the term of this patent is extended or adjusted under 35 U.S.C. 154(b) by 387 days.

(21) Appl. No.: 15/570,979

(22) PCT Filed: May 12, 2016

(86) PCT No.: PCT/EP2016/060781
§ 371 (c)(1),
(2) Date: Oct. 31, 2017

(87) PCT Pub. No.: WO2016/180949
PCT Pub. Date: Nov. 17, 2016

(65) Prior Publication Data
US 2019/0038827 A1    Feb. 7, 2019

Related U.S. Application Data

(60) Provisional application No. 62/160,736, filed on May 13, 2015.

(51) Int. Cl.
*A61M 1/36* (2006.01)
*A61M 60/113* (2021.01)
*A61M 60/279* (2021.01)

(52) U.S. Cl.
CPC ........ *A61M 1/3666* (2013.01); *A61M 1/3667* (2014.02); *A61M 60/113* (2021.01); *A61M 60/279* (2021.01); *A61M 2209/086* (2013.01)

(58) Field of Classification Search
CPC .............. A61M 1/3666; A61M 1/3667; A61M 1/1006; A61M 1/1039; A61M 1/3633;
(Continued)

(56) References Cited

U.S. PATENT DOCUMENTS 6,071,258 A    6/2000  Dalke et al.
2002/0176798 A1 * 11/2002  Linker ................ A61M 1/3627
                                                            422/45
(Continued)

FOREIGN PATENT DOCUMENTS

CN    101563120 A    10/2009
CN    101986776 A    3/2011
(Continued)

OTHER PUBLICATIONS

International Search Report and Written Opinion dated Jul. 20, 2016, in corresponding International Patent Application No. PCT/EP2016/060781 filed May 12, 2016 (10 Pages).
(Continued)

*Primary Examiner* — Philip R Wiest
(74) *Attorney, Agent, or Firm* — Wesley Scott Ashton

(57) ABSTRACT

An extracorporeal heart-lung support machine apparatus includes a platform capable of supporting one or more pieces of equipment and at least one coupler mounted to the platform so as to provide a docking interface for a piece of equipment, wherein the coupler includes: an electrical interface configured to matingly engage with a complementary configured electrical interface of the at least one piece of equipment; and a locking mechanism configured to selectively transition between a locked configuration in which a latch member of the locking mechanism is positioned to secure the at least one piece of equipment to the coupler and an unlocked configuration in which the latch member of the locking mechanism is positioned to permit both engagement
(Continued)

or disengagement of the electrical interface of the coupler with the electrical interface of the at least one piece of equipment.

22 Claims, 12 Drawing Sheets

(58) Field of Classification Search
CPC .......... A61M 1/3663; A61M 2209/086; A61M 60/113; A61M 60/279
See application file for complete search history.

(56) References Cited

U.S. PATENT DOCUMENTS

| | | | |
|---|---|---|---|
| 2005/0095152 A1 | 5/2005 | Dale | |
| 2008/0077068 A1* | 3/2008 | Orr | F04B 43/025 604/6.11 |
| 2008/0149551 A1* | 6/2008 | Brugger | A61M 1/3441 210/232 |
| 2009/0115199 A1 | 5/2009 | Dale | |
| 2015/0073335 A1 | 3/2015 | Muller-Spanka et al. | |

FOREIGN PATENT DOCUMENTS

| | | |
|---|---|---|
| CN | 103089085 A | 5/2013 |
| CN | 103625313 A | 3/2014 |
| CN | 103796709 A | 5/2014 |
| CN | 104203334 A | 12/2014 |
| CN | 104481313 A | 4/2015 |
| CN | 104602618 A | 5/2015 |
| CN | 104602636 A | 5/2015 |
| JP | 201446026 A | 3/2014 |
| JP | 2015167720 A | 9/2015 |
| WO | 2009055639 A2 | 4/2009 |
| WO | 2016180949 A1 | 11/2016 |

OTHER PUBLICATIONS

Compression Latch (Southco), at http://www.southco.com/static/Literature/62.en.pdf (downloaded Apr. 21, 2015).
Headstone Shapes, at http://www.monuments-of-distinction.com/id21.html (downloaded Mar. 27, 2015).
Chinese Office Action (with English translation) and Chinese Search Report dated Dec. 2, 2019 during the prosecution of corresponding Chinese Patent Application No. 201680027842.3, 9 pages.
Official Action issued in Japanese Application No. 2017-558688 dated Apr. 1, 2020, 9 pages.
The American Heritage Desk Dictionary 724 (1981).
Notification to Grant Patent Right for Invention and Search Report issued in counterpart Chinese Application No. 201680027842.3 dated Jun. 2, 2020, 6 pages. English Translation for only Notification to Grant Patent Right for Invention provided.
International Preliminary Report on Patentability issued in International Application No. PCT/EP2016/060781 dated Nov. 23, 2017, 7 pages.

* cited by examiner

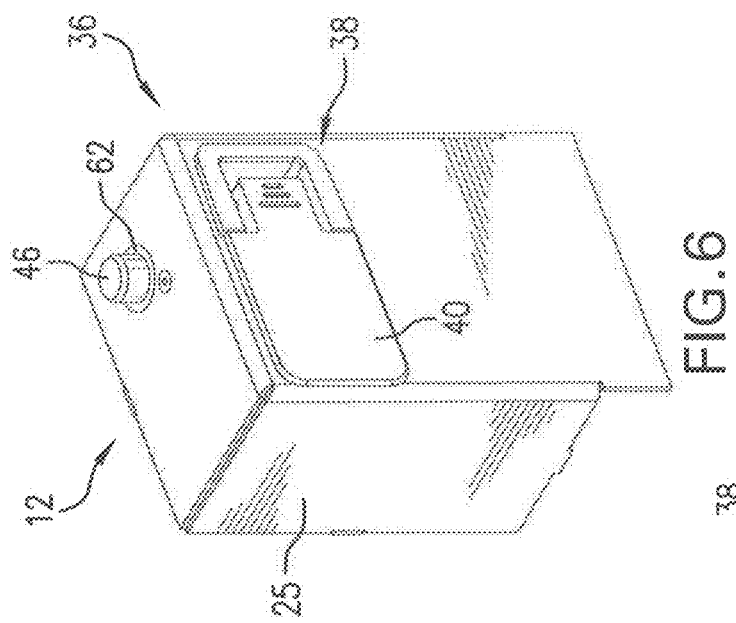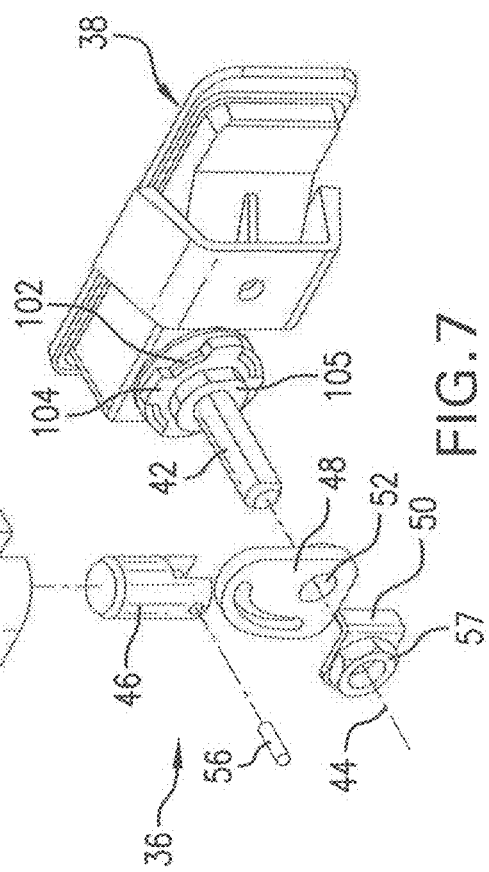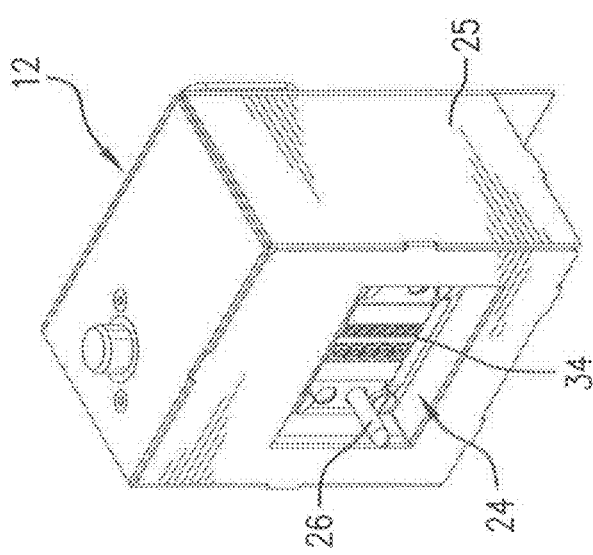

EQUIPMENT DOCKING INTERFACE WITH LATCH MECHANISM FOR HEART-LUNG MACHINE

This application is a national stage entry (under 35 USC 371) of PCT/EP/2016060781, filed May 12, 2016, which claims the benefit of priority to U.S. Provisional Patent Application 62/160,736, filed May 13, 2015, the disclosure of which are hereby incorporated by reference in their entirety.

FIELD OF THE DISCLOSURE

This disclosure pertains broadly to a docking mechanism or interface, such as a pump latch mechanism, of a heart-lung machine or other cardio-pulmonary bypass system, which is employed so connect a peristaltic heart pump, or other electromechanical device (equipment), to its proper position or seat within the heart-lung machine or other cardiopulmonary bypass system.

BACKGROUND OF THE DISCLOSURE

There is an ever evolving need for docking interfaces that can be used to mount one kind of electromechanical device to another kind of electromechanical device. For example, in the field of heart-lung machines, various electromechanical devices, such as a cardiac pump (e.g., a peristaltic pump) and other apparatuses, are mounted to a frame of a heart-lung machine via individual docking interfaces. However, such docking interfaces have exhibited certain disadvantages. For example, some docking interfaces include an electronic interface for power and signal connections, wherein the electronic interface is positioned to engage the underbelly of a peristaltic pump. Peristaltic pumps are heavy, so there has been a tendency for the peristaltic pumps to compress and damage electronic interfaces located on their underbelly.

Another disadvantage of prior art docking interfaces is that it is difficult to view the docking interface when connecting a cardiac pump to the electronic interface of the docking interface. As a result, those assembling or re-arranging one or more cardiac pumps on the frame of a heart-lung machine cannot see whether a cardiac pump is properly aligned to dock with the electronic interface. This makes it more difficult to properly connect the cardiac pump to the docking interface and increases the likelihood that the electronic interfacing components (e.g., plugs, sockets, etc.) of the docking interface will be damage due to attempts to connect misaligned components of the docking interface.

A further disadvantage of prior art docking interfaces is that they are not constructed to permit "hot" swappability, which means that one or more cardiac pumps or other devices cannot be swapped while the heart-lung machine is operating.

SUMMARY

In accordance with a first non-limiting, illustrative embodiment of this disclosure, an extracorporeal heart-lung support machine apparatus is provided that has a platform capable of supporting one or more pieces of equipment and at least one coupler mounted to the platform so as to provide a docking interface for a piece of equipment, wherein the coupler includes: an electrical interface configured to matingly engage with a complementary configured electrical interface of the at least one piece of equipment; and a locking mechanism configured to selectively transition between a locked configuration in which a latch member of the locking mechanism is positioned to secure the at least one piece of equipment to the coupler and an unlocked configuration in which the latch member of the locking mechanism is positioned to permit both engagement or disengagement of the electrical interface of the coupler with the electrical interface of the at least one piece of equipment. Such an embodiment is capable of hot swappability during operation of the extracorporeal heart-lung support machine apparatus, which means that the at least one piece of equipment can be swapped out and replaced with another equivalent piece of equipment while the extracorporeal heart-lung support machine apparatus is operating. In accordance with a second non-limiting, illustrative embodiment of this disclosure, the first non-limiting embodiment is modified so that the at least one piece of equipment is a cardiac pump.

In accordance with a third non-limiting, illustrative embodiment of this disclosure, the first and second non-limiting embodiments are modified so that the platform comprises at least one rail arranged with respect to the at least one coupler so that a track disposed on a bottom surface of the at least one piece of equipment is engageable with the at least one rail so as to slide on the at least one rail. In accordance with a fourth non-limiting, illustrative embodiment of this disclosure, the first, second and third non-limiting embodiments are further modified so that the locking mechanism includes a latch assembly that is connected to move the latch member between a retracted position and an extended position, wherein in the extended position the latch member is capable of engaging a stop of the at least one piece of equipment.

In accordance with a fifth non-limiting illustrative embodiment of this disclosure, the fourth non-limiting embodiment is modified so that the latch assembly comprises a lever attached by a pivot pin to one end of a shaft so that the lever pivots with respect to the shaft and so that rotation of the lever about an axis of the shaft rotates the shaft about the axis. In accordance with a sixth non-limiting illustrative embodiment of this disclosure, the fourth and fifth non-limiting embodiments are further modified so that a spring is disposed on the shaft so as to exert a force on the lever via the shaft. In accordance with a seventh non-limiting illustrative embodiment of this disclosure, the fourth, fifth and sixth non-limiting embodiments are further modified so that the lever is moveable from a substantially horizontal unsecured position to a substantially vertical unsecured position, and from the substantially vertical unsecured position to a substantially vertical secured position. In accordance with an eighth non-limiting illustrative embodiment of this disclosure, the fourth, fifth, sixth and seventh non-limiting embodiments are further modified so that the lever comprises a body portion that has a roughly rectangular shape with a side end separated from a side floor by a rounded edge so as to provide a cam surface, wherein the cam surface provides a fulcrum so force exerted on the lever compresses the spring when the lever moves from the unsecured vertical position to the secured vertical position. In accordance with a ninth non-limiting, illustrative embodiment of this disclosure, the fourth, fifth, sixth, seventh and eighth non-limiting embodiments are further modified so that rotation of the lever about the axis of the shaft is constrained to a quarter turn that moves the lever from the substantially horizontal unsecured position to the substantially vertical unsecured position. In accordance with a tenth non-limiting illustrative embodiment of this disclosure, the fourth, fifth, sixth, seventh, eighth and ninth non-limiting embodiments are further modified so that pivoting the lever about 90 degrees about the pivot pin moves the lever from the substantially vertical unsecured position to the substantially vertical secured position.

In accordance with an eleventh non-limiting illustrative embodiment of this disclosure, the fourth, fifth, sixth, seventh, eighth, ninth and tenth non-limiting embodiments are further modified so that the lever further comprises a paddle attached to the body portion. In accordance with a twelfth non-limiting, illustrative embodiment of this disclosure, the fourth, fifth, sixth, seventh, eighth, ninth, tenth and eleventh non-limiting embodiments are further modified so that when the lever is in the substantially vertical secured position, the paddle is substantially flush with a rim of a well of the locking mechanism.

In accordance with a thirteenth non-limiting illustrative embodiment of this disclosure, the filth, sixth, seventh, eighth, ninth, tenth, eleventh and twelfth non-limiting embodiments are further modified so that the latch member comprises a latch pin, and a cam connects the latch pin to the shaft so that rotation of the lever from the substantially horizontal unsecured position to the substantially vertical unsecured position causes the latch pin to move to the extended position through a latch pin guide device. In accordance with a fourteenth non-limiting illustrative embodiment of this disclosure, the thirteenth non-limiting embodiment is further modified so that when the lever moves from the substantially vertical unsecured position to the substantially vertical secured position, the cam moves toward the lever and the spring is compressed on the shaft. In accordance with a fifteenth non-limiting illustrative embodiment of this disclosure, the thirteenth and fourteenth non-limiting embodiments are further modified so that the latch pin guide device includes a seal member that provides a seal between the latch pin guide device and the latch pin.

In accordance with a sixteenth non-limiting illustrative embodiment of this disclosure, the fifth, sixth, seventh, eighth, ninth, tenth, eleventh and twelfth non-limiting embodiments am further modified so that the latch member comprises a latch bar having a flat profile. In accordance with a seventeenth non-limiting illustrative embodiment of this disclosure, the sixteenth non-limiting embodiment is further modified so that the latch bar is connected so as to rotate with the shaft so that rotation of the lever from the substantially horizontal unsecured position to the substantially vertical unsecured position causes the latch bar to move to the extended position through a linear orifice formed in a housing of the coupler. In accordance with an eighteenth non-limiting illustrative embodiment of this disclosure, the sixteenth and seventeenth non-limiting embodiments are modified to further include a seal device disposed to provide a seal at the linear orifice that is penetrable by the latch bar when the latch bar moves from the retracted position to the extended position.

In accordance with a nineteenth non-limiting, illustrative embodiment of this disclosure, a method of docking a peristaltic pump to a heart-lung machine apparatus is provided, wherein the method includes the steps of: disposing a coupler mounted to a platform of a heart-lung machine apparatus into a matingly shaped recess of a housing of the pump so that the pump rests on the platform, wherein the coupler includes an electrical interface and a locking mechanism that is in an unlocked configuration; axially rotating a lever of the locking mechanism from an unsecured first position to an unsecured second position so that a latch pin is moved from a non-latching position in which the latch pin does not substantially engage a stop of the housing of the pump to a latching position in which the latch pin substantially engages a stop of the housing of the pump, thereby locking the coupler and the pump together; and moving the lever from the unsecured second position to a secured position in which the lever is substantially flush with an external rim of a well of the locking mechanism. In accordance with a twentieth non-limiting, illustrative embodiment of this disclosure, a method of docking a peristaltic pump to a heart-lung machine apparatus is provided, wherein the method includes the steps of: disposing a coupler mounted to a platform of a heart-lung machine apparatus into a matingly shaped recess of a housing of the pump so that the pump rests on the platform, wherein the coupler includes a housing, an electrical interface, and a locking mechanism that is in an unlocked configuration, wherein the electrical interface and the locking mechanism are disposed at least partially within the housing of the coupler; axially rotating a lever of the locking mechanism from an unsecured first position to an unsecured second position so that a latch bar is moved from a non-latching position in which the latch bar does not substantially engage a stop of the housing of the pump to a latching position in which the latch bar loosely or lightly engages a stop of the housing of the pump, thereby locking the coupler and the pump together; moving the lever from the unsecured second position to a secured position in which the lever is substantially flush with an external rim of a well of the locking mechanism; and moving the latch bar from a forward position to a rearward position within a linear orifice of the housing of the coupler so that a tip of the latch bar exerts increased pressure against the stop of the pump when the lever moves from the unsecured second position to the secured position.

BRIEF DESCRIPTION OF THE DRAWINGS

The following descriptions should not be considered limiting in any way. It is to be appreciated that directions or relative positions, such as front, back, side, top, bottom, up, down, etc., as used herein are for the sake of discussion only with respect to the orientation shown in the Figures and should in no way be considered limiting. With reference to the accompanying drawings, like elements are numbered alike:

FIG. 5 is a front perspective view of a coupler according to an embodiment of this disclosure.

FIG. 6 is a rear perspective view of the coupler of FIG. 5.

FIG. 7 is an exploded view of a locking mechanism according to the coupler embodiment shown in FIG. 5.

FIGS. 12A, 12B, 12C and 12D (collectively referable to as "FIG. 12") illustrate various positions of a lever of a latch assembly of a coupler embodiment according to FIGS. 5 and 6, wherein FIG. 12A illustrates the lever in an unsecured horizontal position, FIG. 12B illustrates the lever in an unsecured intermediate position, FIG. 12C illustrates the lever in an unsecured vertical position, and FIG. 12D illustrates the lever in a secured vertical position.

FIGS. 16A, 16B, 16C and 16D (collectively referable to as "FIG. 16") illustrate various positions of a lever of a latch assembly of a coupler embodiment according to FIG. 15, wherein FIG. 16A illustrates the lever in an unsecured horizontal position. FIG. 16B illustrates the lever in an unsecured intermediate position, FIG. 16C illustrates the lever in an unsecured vertical position, and FIG. 16D illustrates the lever in a secured vertical position.

FIGS. 17A and 17B (collectively referable to as "FIG. 17") illustrate various positions of a latch bar of a coupler embodiment according to FIG. 14, wherein FIG. 17A illustrates the forward position of the latch bar when the lever in an unsecured vertical position, and FIG. 17B illustrates the rearward position of the latch bar when the lever is in the secured vertical position.

DETAILED DESCRIPTION

A detailed description of one or more embodiments of the disclosed apparatus and method are presented herein by way of exemplification, and not limitation with reference to the Figures. In the Figures, like parts are designated by like reference numbers.

Figure 1:
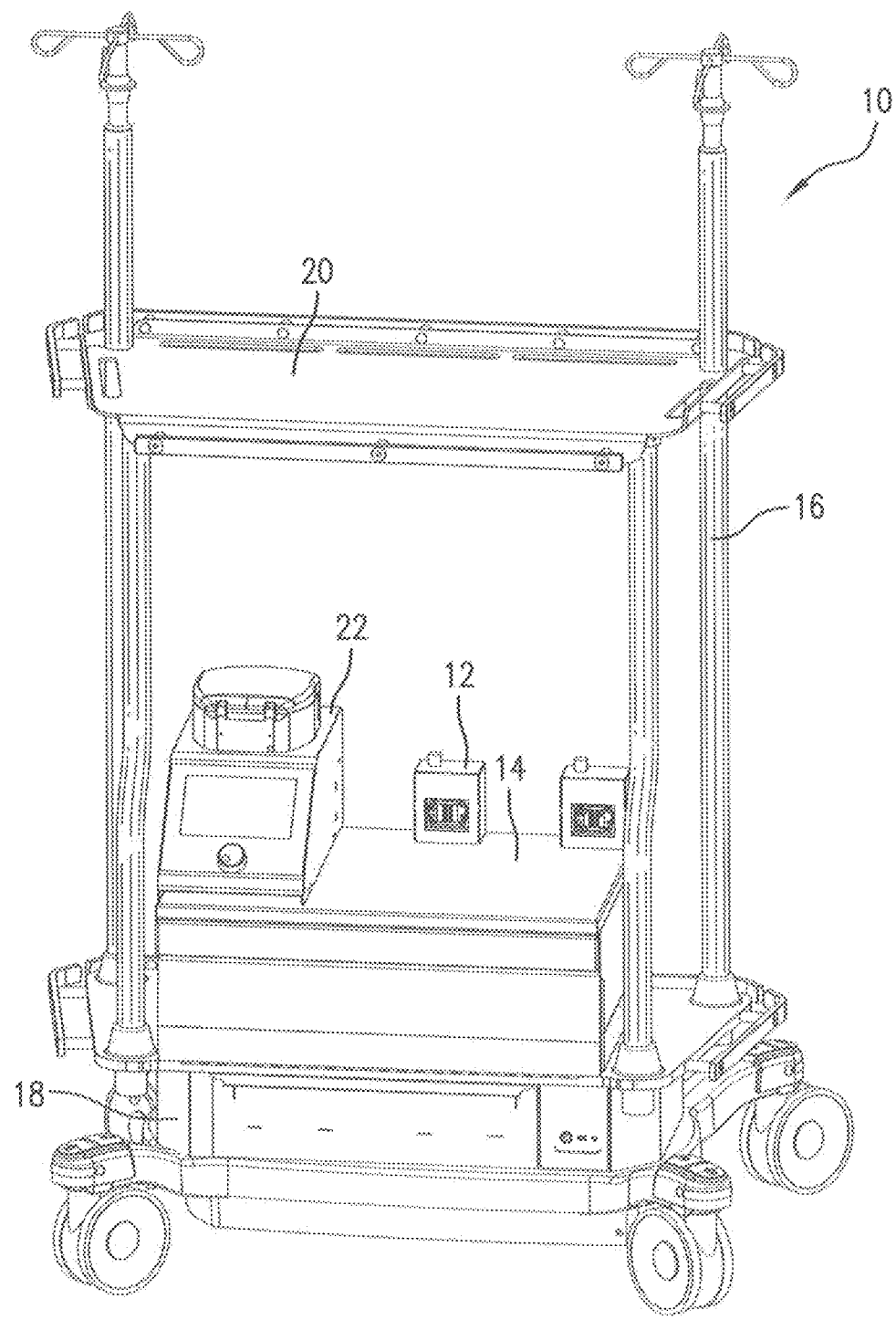
FIG. 1 is a front perspective view of a heart-lung machine apparatus for extracorporeal blood circulation according to an embodiment disclosed herein.
Figure 2:
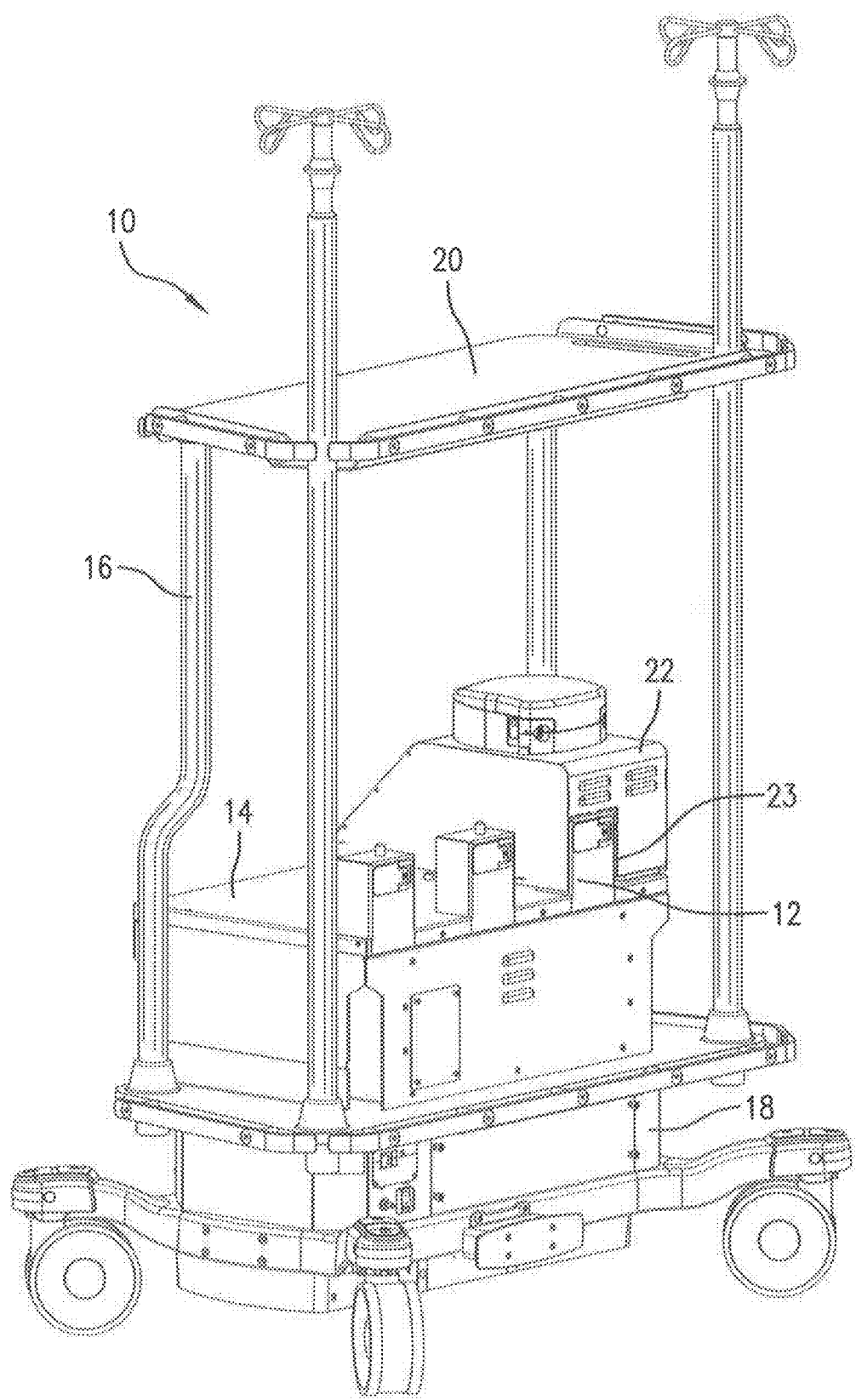
FIG. 2 is a rear perspective view of she heart-lung machine apparatus of FIG. 1.

Referring now to the drawings, an extracorporeal heart-lung support machine apparatus 10 is illustrated in FIGS. 1 and 2. The heart-lung machine apparatus 10 includes one or more docking interfaces, wherein each docking interface includes a coupler 12 mounted on platform 14. In the alternative, the heart-lung machine apparatus 10 may be construed as possessing a single docking interface that includes a plurality of couplers 12 mounted on platform 14. A coupler 12, in accordance with this disclosure, may also be referred to as a coupling unit.

The heart-lung machine apparatus 10 may include any combination of additional components or structures, such as a plurality of masts 16 arranged to mountably receive monitors, pumps, or other accessories thereon, a trolley 18 on which the platform 14 is mounted in order to impart rolling mobility to the heart-lung machine apparatus 10, an upper tray 20 to provide a user, such as a perfusionist, with additional surface area for positioning other kinds of pumps and/or monitors that may be employed as components of an extracorporeal cardio-pulmonary bypass system.

Each of the couplers 12 is arranged to receive and selectively mechanically and/or electrically couple a corresponding piece of equipment, such as a peristaltic pump 22, to the heart-lung machine apparatus 10. In the embodiment illustrated in FIGS. 1 and 2, the heart-lung machine apparatus 10 includes three couplers 12 mounted on the platform 14, with a pump 22 sitting on the platform 14 and coupled to one of the couplers 12. Of course, each of the couplers 12 may be coupled to a single pump 22, so that three pumps 22 are coupled on the platform 14 to three couplers 12. In other words, there is a one-to-one correspondence for the couplers 12 to pumps 22.

The pump 22 may include a monitor or display, controls, etc., to enable a user to interact with and/or control the operation of the pump. Each of the couplers 12 may be correspondingly attached to its own pump 22. As evident from FIG. 2, each coupler 12 constitutes a post or protrusion extending from the platform 14, and is configured to matingly engage a correspondingly configured recess 23 formed in the housing of the pump 22. While the couplers 12 may be generally rectangular in shape so as to mate with a generally rectangular shaped recess 23 formed in the housing of the pump, other mating shapes for the couplers 12 and recesses 23 may be employed. For example, the couplers 12 and recesses 23 may employ suitable mating shapes selected from the group consisting of square shapes, triangular shapes, semi-circular shapes and tombstone shapes (see, e.g., http://www.monuments-of-distinction.com/id21.html).

It is to be understood that any number of the couplers 12 may be mounted on platform 14, and that any corresponding number of pumps may be engaged via mating recesses 23 with respective couplers 12. Thus, each coupler 12 may connect to a pump 22, although not all of the couplers 12 need to be connected to a corresponding pump 22 for the heart-lung machine apparatus 10 to be operational. Thus, it is within the scope of this disclosure to provide only one coupler 12 on the platform 14, although it is also within the scope of this disclosure to provide two couplers 12 on the platform 14, or three couplers 12 on the platform 14, or four couplers on the platform 14, or five couplers 12 on the platform 14, or six couplers 12 on the platform 14, and so on. In an embodiment, a plurality of couplers 12 form an array of docking posts or docking protrusions extending upwards from the surface of the platform 14, and which are located along a rear edge of the platform 14.

Figure 14:
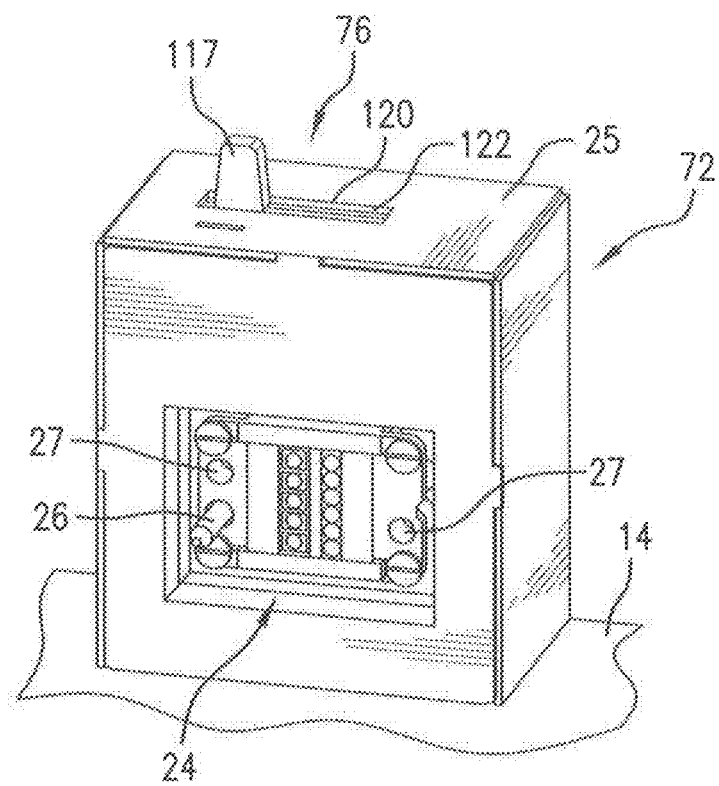
FIG. 14 is a front perspective view of a coupler according to another embodiment of this disclosure.
Figure 15:
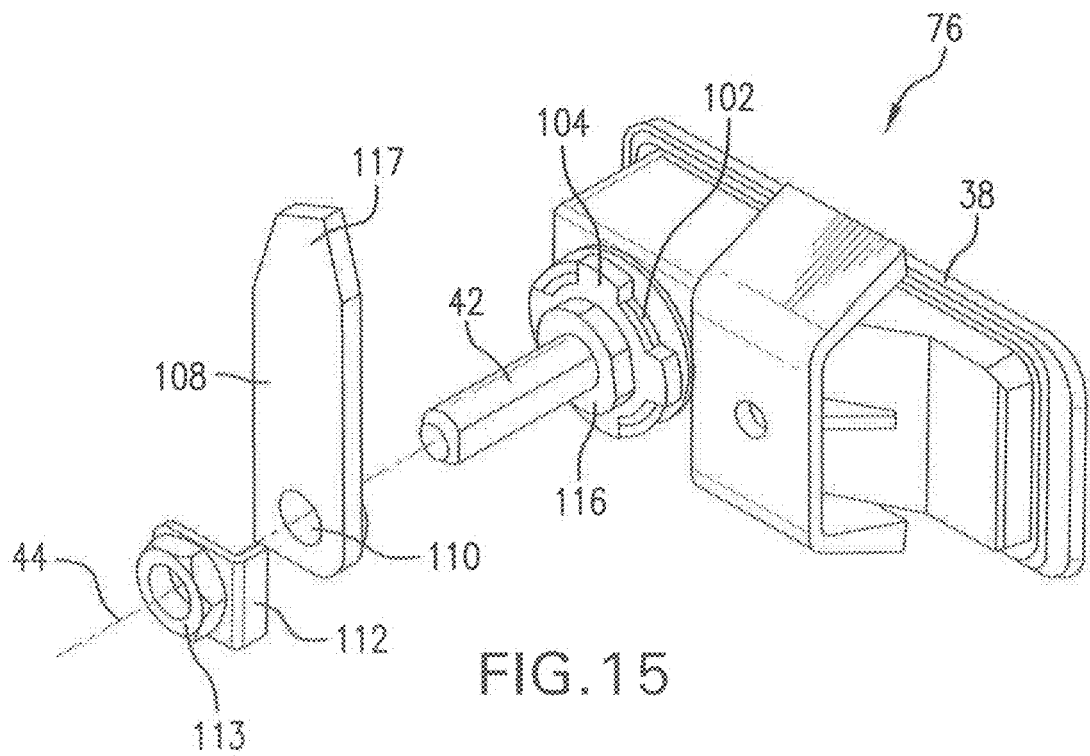
FIG. 15 is an exploded view of a locking mechanism according to the coupler embodiment shown in FIG. 14.

One of the couplers 12 is illustrated in more detail in FIGS. 5 and 6. The coupler 12 has a housing 25, and includes an electrical interface 24 configured to electrically couple a piece of equipment, such as the pump 22, to the heart-lung machine apparatus 10 via a corresponding electrical interface 124 of the piece of equipment. The electrical interface 24 may include one or more pins 26 to facilitate mechanical or electro-mechanical coupling of the pump 22 to the heart-lung machine apparatus 10 and alignment of the pump 22 with the electrical interface 24 because the pump 22 is provided with corresponding receiving structures, such as holes, recesses or channels formed in the pump housing or in the pump's electrical interface, which may matingly engage the one or more pins 26. The one or more pins 26 may function as guiding pins to facilitate proper coupling between the electrical interface 24 and electrical interface 124 of the pump 22. As shown in FIG. 14, in accordance with some embodiments of this disclosure, the electrical interface 24 may include one or more receiving structures 27, such as holes, recesses or channels formed in the housing 25, which may engage a corresponding number of pins connected to the housing of the pump 22. The one or more receiving structures 27 may function as guiding structures to facilitate proper coupling between the electrical interface 24 and the electrical interface 124 of the pump 22.

More specifically, the pump 22 is able to be engaged with the coupler 12 by placing the pump 22 on the platform 14 and sliding the pump 22 toward the coupler 12. The one or more pins 26, when engaged in corresponding receiving structures of the pump 22, help prevent side-to-side movement of the pump 22 with respect to the coupler 12 and, in addition, one or more pins 26 may be electrically conductive in order to enable electrical signals and/or power to be transferred therethrough. Likewise, the one or more receiving structures 27, when engaged with corresponding pins of the pump 22, may help prevent side-to-side movement of the pump 22 with respect to the coupler 12. In an embodiment of this disclosure, one or more receiving structures 27 may be electrically conductive in order to enable electrical signals and/or power to be transferred therethrough.

Figure 3:
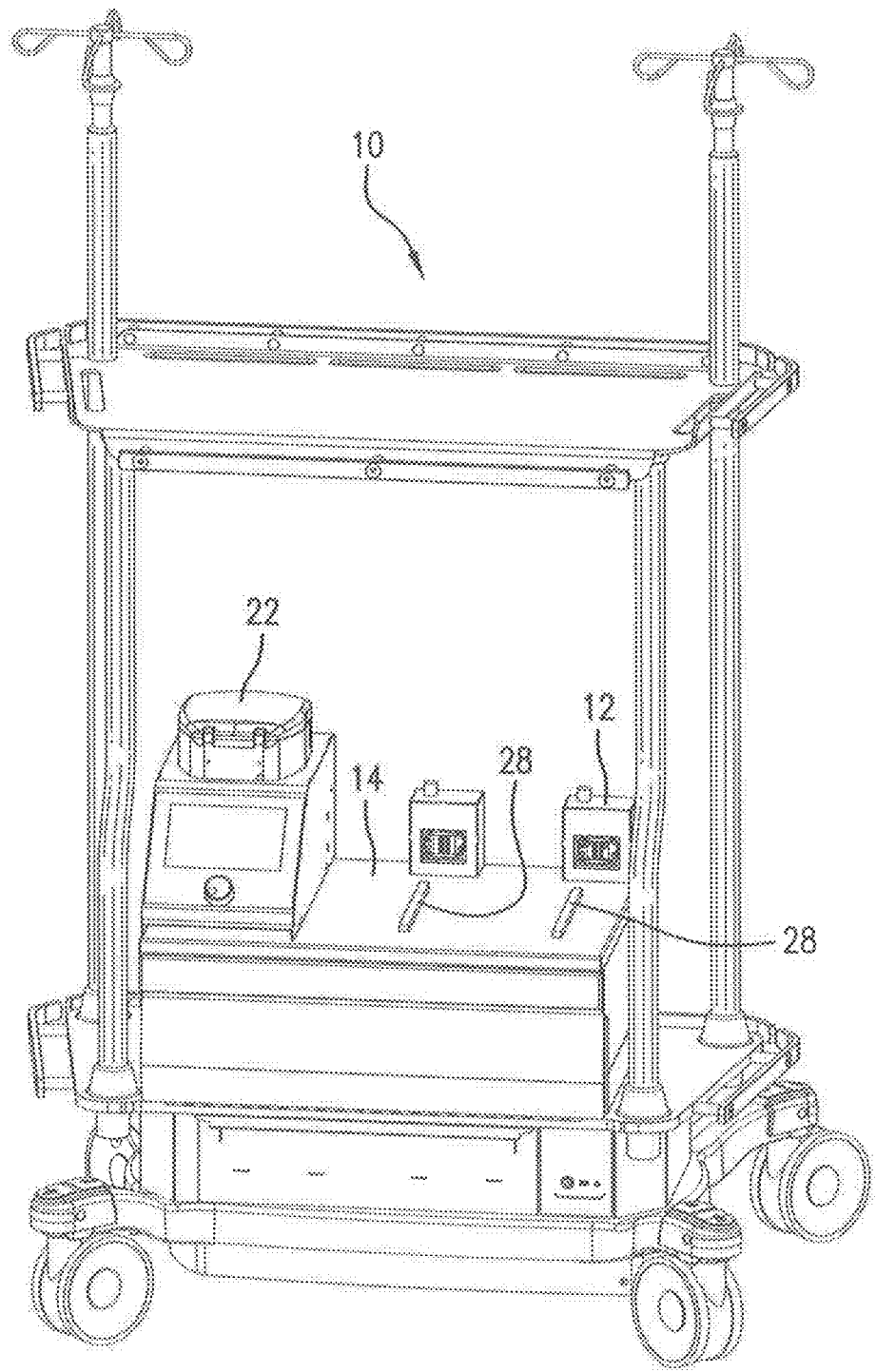
FIG. 3 is a front perspective view of a heart-lung machine apparatus according to an embodiment disclosed herein, generally resembling the heart-lung machine apparatus of FIG. 1, but additionally including one or more side rails for assisting in the alignment and installation of pumps thereon.
Figure 4:
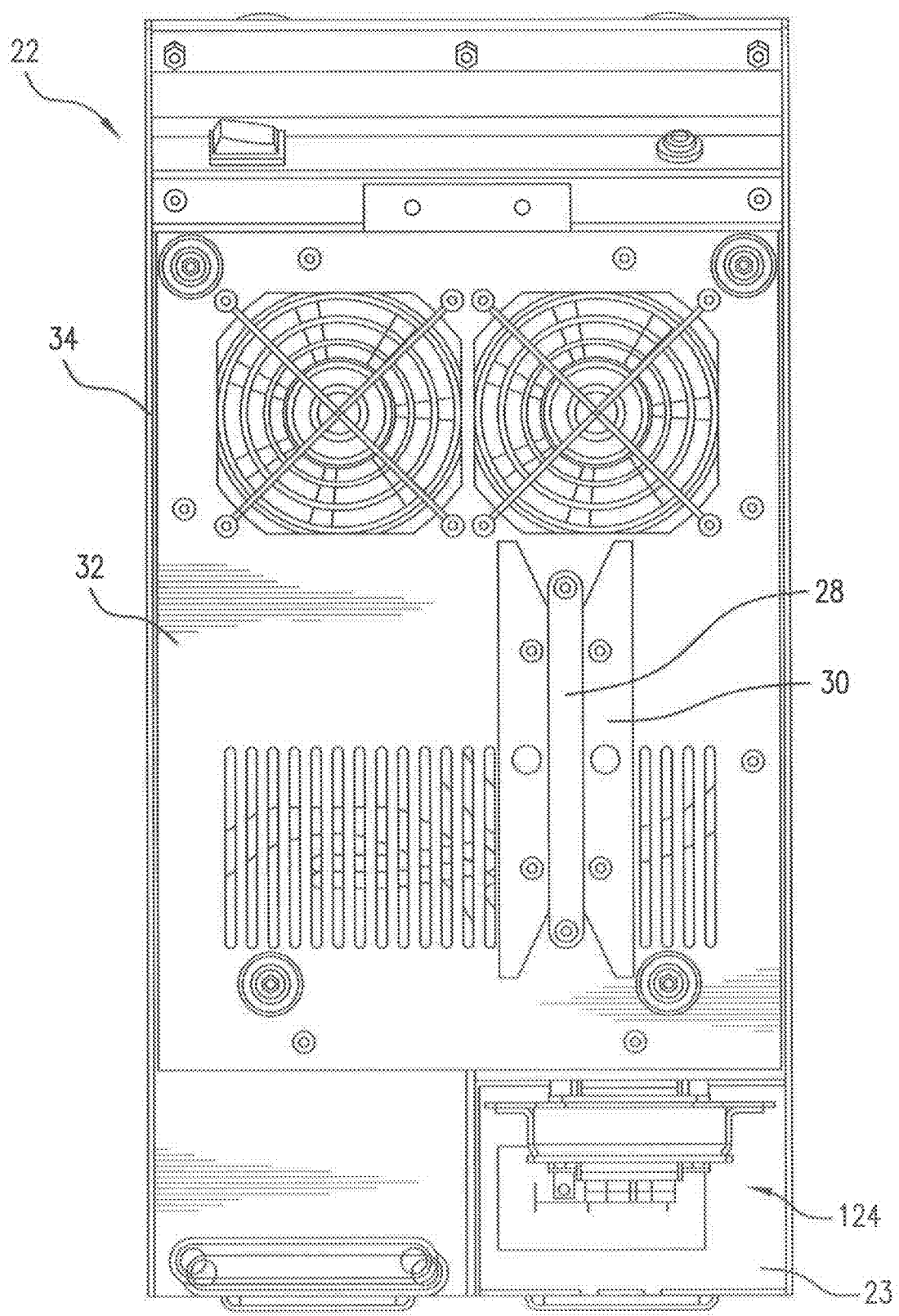
FIG. 4 is a bottom view of a pump showing a slide rail of the heart-lung machine of FIG. 3 engaged therewith.

As shown in FIGS. 3 and 4, in an embodiment of this disclosure the platform 14 may be optionally provided with rails 28 that may each engage a rail track 30 formed in, or attached to, a bottom portion 32 of the housing 35 of pump 22. Each rail 28, when matingly engaged with a rail track 30, stabilizes the pump 22 associated therewith on the platform 14 and facilitates coupling between pump 22 and coupler 12.

The electrical interface 24 also includes an array 34 of electrical connectors, either all male electrical connectors or all female electrical connectors or a combination of male and female electrical connectors, which matingly engage respectively with all female electrical connectors or all male electrical connectors or a combination of female and male electrical connectors, which are components of an electrical interface 124 of the pump 22. In this way, when pump 22 is coupled to coupler 12, a plurality of electrical connections are established by the electrical interface 24 connected to the electrical interface 124 of the pomp 22 so that the pump 22 may send signals to one or more devices of the heart-lung machine apparatus 10 that monitor the operation of the pump 22, and so the pump 22 may receive signals from one or more devices of the heart-lung machine apparatus 10 that control and/or affect operation of the pump 22.

Each coupler 12 is provided with a locking mechanism 36, which is included in order to selectively restrict and allow relative movement between the coupler 12 and the pump 22 as the locking mechanism 36 transitions between locked and unlocked configurations, respectively. An embodiment of the locking mechanism 36 is illustrated in more detail in FIGS. 6-11.

Figure 8:
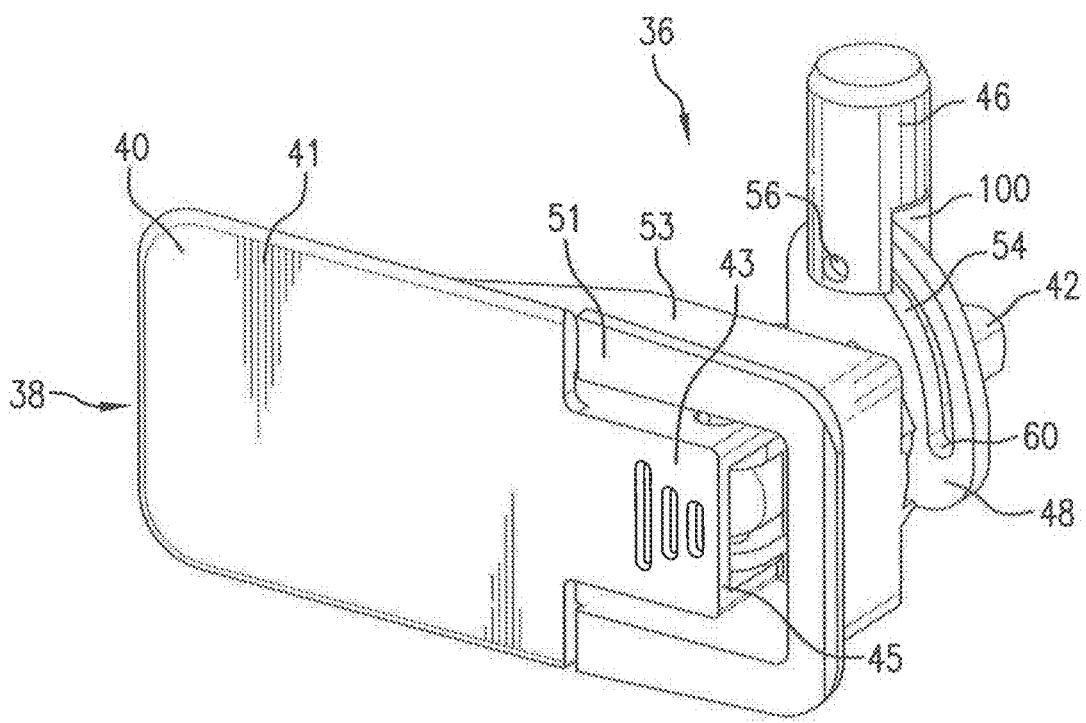
FIG. 8 is a perspective view of a portion of the locking mechanism of FIG. 7, shown in a locked configuration.
Figure 9:
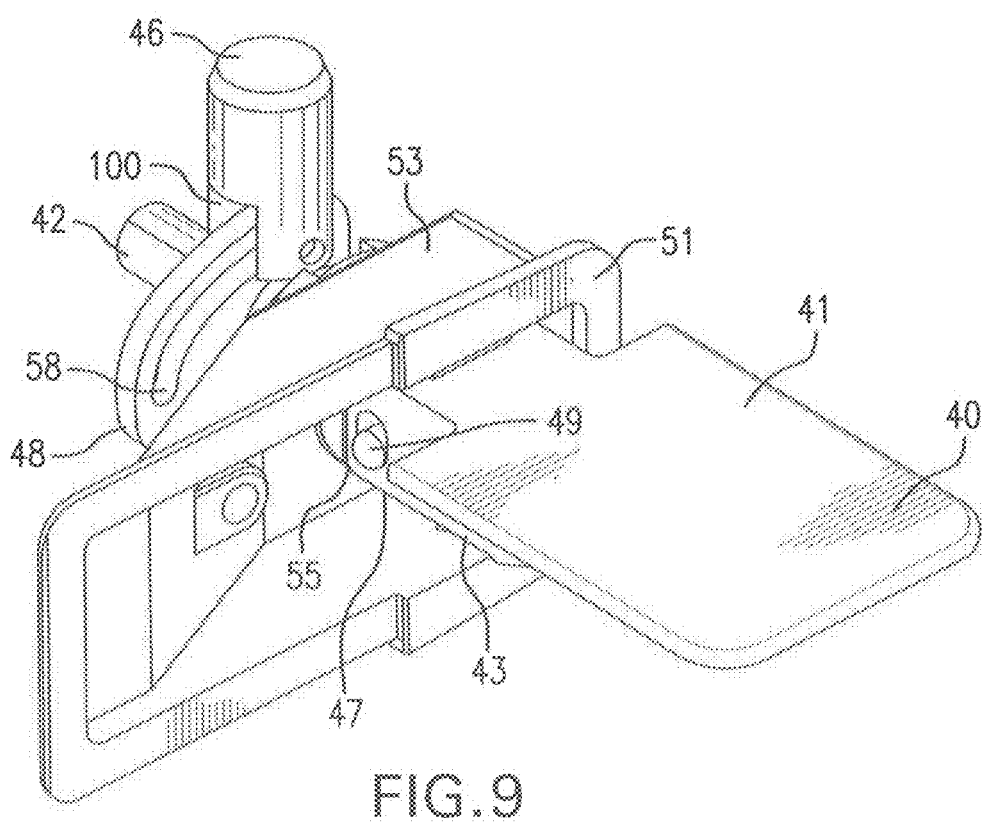
FIG. 9 is a perspective view of the portion of the locking mechanism of FIG. 8, shown in an unlocked configuration.
Figure 10:
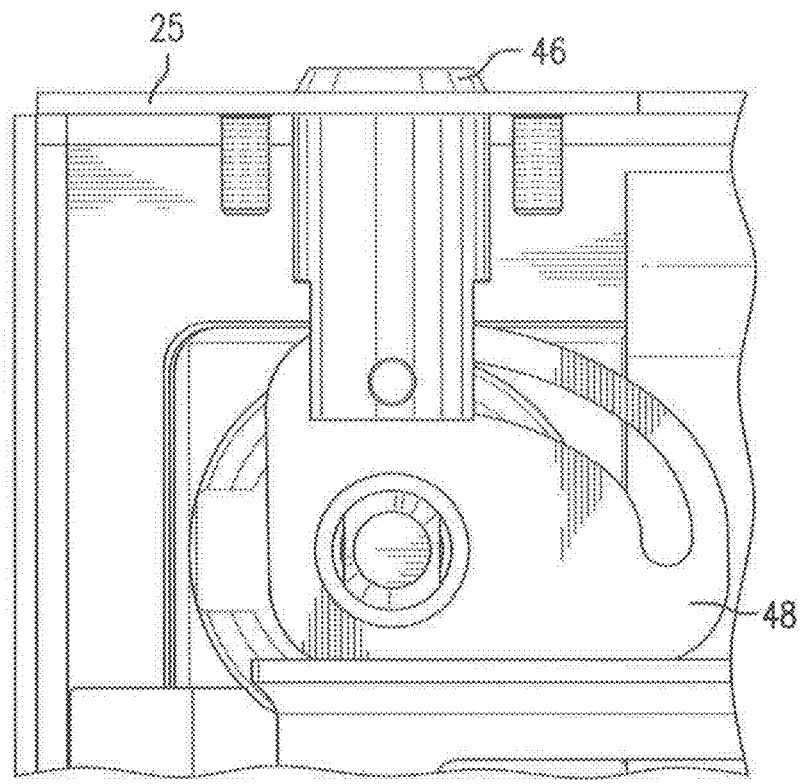
FIG. 10 is an internal view of a portion of the locking mechanism of FIG. 9, when in the unlocked configuration.
Figure 11:
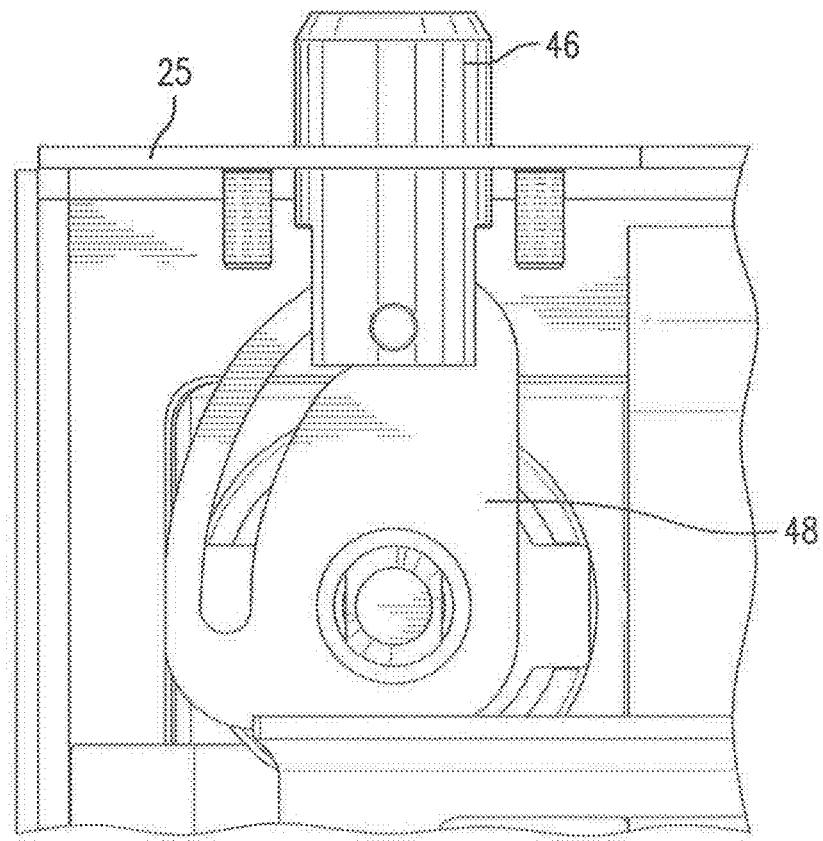
FIG. 11 is an internal view of a portion of the locking mechanism of FIG. 8, when in the locked configuration.
Figure 12A:
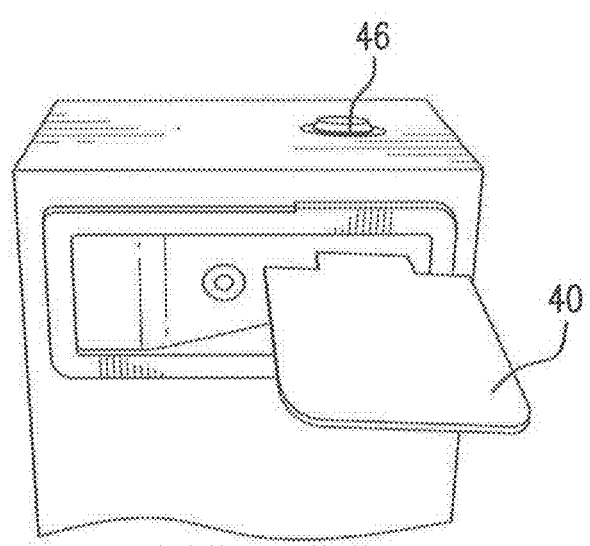
Figure 12B:
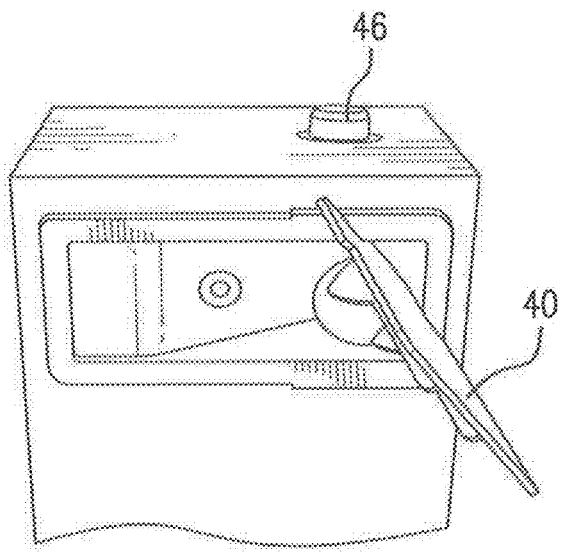
Figure 12C:
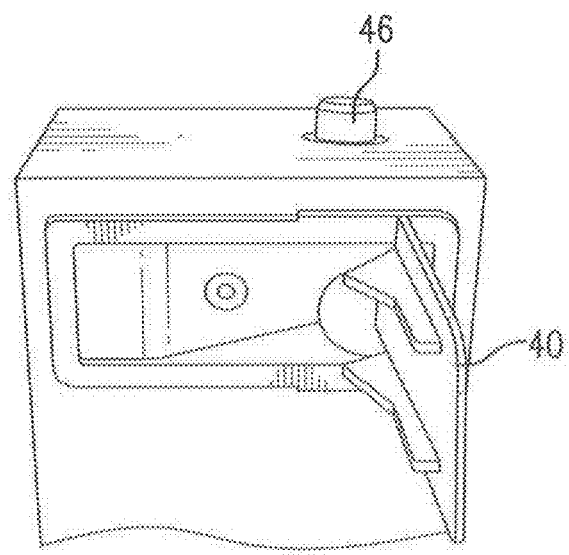
Figure 12D:
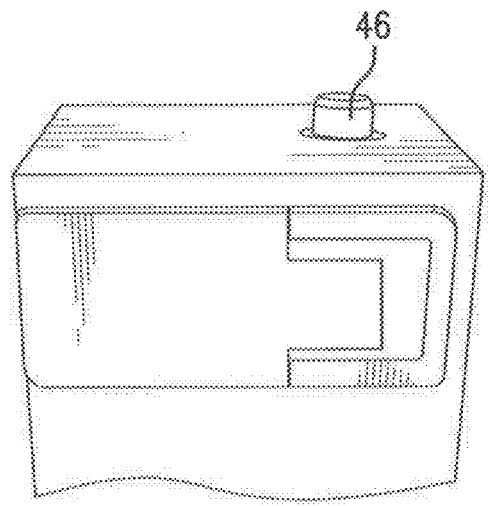
Figure 13:
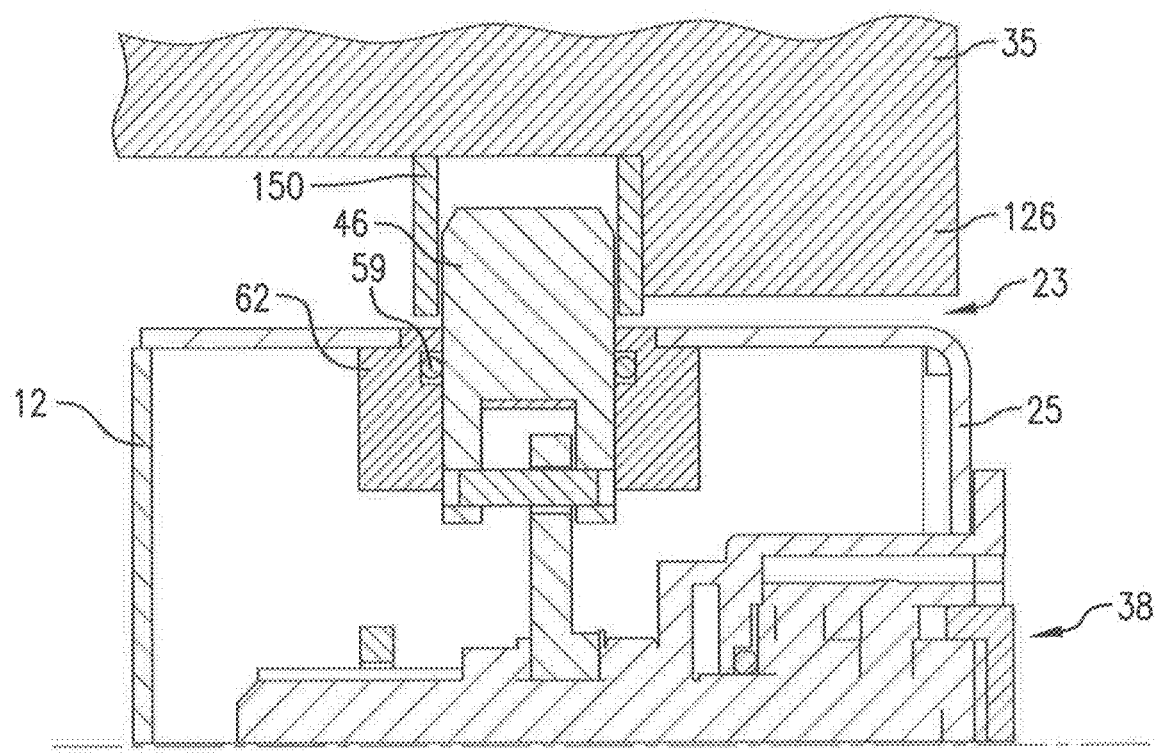
FIG. 13 is a schematic cross-sectional view illustrating potential engagement of a latch pin of the locking mechanism of a coupler with a stop of a housing of a piece of equipment in accordance with an embodiment of this disclosure.

More specifically, the locking mechanism 36 includes a latch assembly 38 connected to move a latch pin 46 with respect to the coupler 12 so as to transition the locking mechanism 36 between its locked configuration, as shown in FIGS. 6, 8 and 11, and its unlocked configuration, as shown in FIGS. 10 and 12A. The latch assembly 38 includes a lever 40 that is mounted to cause rotation of a shaft 42 when the lever 40 is rotated with respect to the rotational axis 44 of the shaft 42 as evident from FIGS. 8 and 9. The lever 40 can be transitioned between a secured vertical position, at which rotation of the lever 40 about the axis 44 of the shaft 42 is not possible, e.g., as illustrated in FIGS. 6, 8 and 12D, and an unsecured vertical position in which rotation of the lever 40 about the axis 44 of the shaft 42 is possible, e.g., as illustrated in FIG. 12C. Movement of the lever 40 from the unsecured vertical position (FIG. 12C) to an unsecured horizontal position (FIG. 12A) by rotation causes a latch pin 46 of the locking mechanism 36 to move from a maximally extended position (FIGS. 11 and 12C) to a maximally retracted position (FIGS. 10 and 12A). The latch pin 46, when in the maximally extended position (FIGS. 11 and 12C), can lock the pump 22 to the coupler 12 by engaging a stop 126 formed as part of the housing 35 of the pump 22, as shown in FIG. 13, when the coupler 12 is properly positioned in the recess 23 of the pump housing 35. In accordance with an embodiment of this disclosure, when the latch pin 46 is maximally extended, the latch pin 46 is inserted in a bushing 150 attached to the housing 35, and the latch pin 46 may be provided with a bevel at its distal edge in order to facilitate insertion of the latch pin 46 into the bushing 150.

In one embodiment, a cam 48 is mounted to the shaft 42 so that rotation of the shaft 42, e.g., via the lever 40, causes rotation of the cam 48. The cam 48 may be formed as a protrusion of the shaft 40 by casting or molding, or it may be attached or affixed to the shaft 48, e.g., via a fastener, welds, friction fit, etc. In the illustrated embodiment of FIG. 7, a retaining clip 50 assists in causing rotation of the cam 48 when the shaft 42 is rotated, and a fastener 57, such as a nut, secures the retaining clip 50 onto the shaft 42. In an embodiment, the shaft 42 may have a polygonal shape that fits matingly into a correspondingly shaped polygonal hole 52 formed in the cam 48 so that the shaft 42 cannot spin in the hole 52. However, in accordance with other embodiments of this disclosure, the shaft 42 may be cylindrical and fit into a correspondingly shaped cylindrical hole in the cam 48.

The cam 48 includes a slot 54 formed therein. A fastening pin 56 extends through the slot 54 and connects one end of the latch pin 46 to the cam 48. The fastening pin 56 is dimensioned so that it can move in the slot 54 along a path that traverses from a first end 58 of the slot 54 to a second end 60 when the lever 40 is rotated so as to rotate the shaft 42. When the fastening pin 56 is in the first end 58 of the slot 54 the latch pin 46 is located at its maximally extended position. When the fastening pin 56 is in the second end 60 of the slot 54 the latch pin is located at its maximally retracted position. The fastening pin 56 is also substantially longer than the thickness of the cam 48 so that the cam 48 is free to move lengthwise along the length of the fastening pin 56 within a slot 100 formed in the one end of the latch pin 46.

In accordance with an embodiment of this disclosure, the locking mechanism 36 may include a latch pin guide device 62 that is attached to the housing 25 of the coupler 12. The latch pin guide device 62 is provided with an orifice 64 formed therein and through which the latch pin 46 may extend and retract. The orifice 64 and the latch pin 46 may be shaped to mate closely with one another. The orifice 64 of the latch pin guide device 62 provides stabilization of the linear movement of the latch pin 46 as it moves between its maximally extended and maximally retracted positions. Furthermore, the latch pin guide device 62 may be provided with an O-ring seat 59, or other seal, that seals the connection between the latch pin 46 and the latch pin guide device 62 in a fluid-tight manner so that liquid, debris, and mixtures of liquid and debris, cannot penetrate the latch pin guide device 62, which prevents contamination of the interior of the coupler 12 with fluids (including bodily fluids), debris and mixtures of fluids and debris.

On the other hand, although the latch pin 46 is stabilized by the latch pin guide device 62 so it substantially moves only to extend and retract through the orifice 64, the cam 48 is free to move in the lengthwise direction along fastening pin 56 within slot 100. Consequently, when the lever 40 moves between the unsecured vertical position (FIG. 12C) to the secured vertical position (FIG. 12D), the lever 40 pulls shaft 42 outwardly (i.e., in a direction away from the interior of the housing 25), which pulls the cam 48 in the same direction against a spring 102. Thus, the lever 40 pulls the cam 48 to move lengthwise on the fastening pin 56 within the slot 100 in a direction towards the rear of the coupler 12 where the lever 40 is located, which causes compression of spring 102. Thus, the latch assembly 38 may be characterized as a draw latch because movement of the actuating lever 40 may cause the cam 48 to be drawn in a particular direction within the slot 100. The latch assembly 38 may also be characterized as a compression latch because movement of the lever 40 from the unsecured vertical position to the secured vertical position involves compression of the spring 102, as well as movement of the cam 48 towards the lever 40 along the fastening pin 56.

In accordance with a method embodiment of this disclosure, a method of docking a piece of equipment, such as a peristaltic pump 22, to a heart-lung machine apparatus 10 includes the steps of: (a) disposing a coupler 12 mounted to a platform 14 of a heart-lung machine apparatus 10 into a matingly shaped recess 23 of a housing of the piece of equipment so that the piece of equipment rests on the platform 14, wherein the coupler 12 includes an electrical interface 24 and a locking mechanism 26 that is in an unlocked configuration; (b) moving (axially rotating) a lever 40 of the locking mechanism 26 from an unsecured first position (e.g., a substantially horizontal position) to an unsecured second position (e.g., a substantially vertical position) so that a latch pin 46 is moved from a non-latching position (e.g., a maximally retracted position) in which the latch pin 46 does not substantially engage a stop 126 of the housing 35 of the piece of equipment to a latching position (e.g., a maximally extended position) in which the latch pin 46 substantially engages a stop 126 of the housing of the piece of equipment, thereby locking the coupler 12 and the piece of equipment together; and (c) moving (e.g., rotating about a pivot axis formed by a pivot pin 49 attached at one end of the lever) the lever 40 from the unsecured second position to a secured position in which the lever 40 is substantially flush with an external rim 51 of a well 53 of the locking mechanism 36. These steps are evident from FIGS. 12A to 12D and 13.

Step (a) of this method may include, in accordance with an embodiment, connecting the electrical interface 24 of the coupler 12 to an electrical interface 124 of the piece of equipment 22 so that the piece of equipment is connected to send and/or receive signals from at least one device of the heart-lung machine apparatus 10, or to send and/or receive signals from at least one device of a cardio-pulmonary bypass system that incorporates the heart-lung machine apparatus 10. In accordance with another method embodiment, the lever 40 includes a paddle portion 41 connected to a body portion 43, wherein the body portion 43 has a roughly rectangular shape with a side end 45 separated from a side floor 42 by a rounded edge 55 so that the distance between the pivot pin 49 and the side floor 47 (when the lever 40 is in the secured vertical position) is larger than the distance between the pivot pin 49 and the side end 45 (when the lever 40 is in any of the unsecured positions shown by FIGS. 12A, 12B and 12C) so that when the lever 40 is pivoted from the unsecured vertical position to the secured vertical position, the surface provided by the side end 45, the rounded edge 55 and the side floor 47 acts as a cam. This cam surface has a shape that effects a snapping transition between the unsecured vertical position and the secured vertical position, and/or vice versa, as resistance to movement gives way abruptly once rotation moves past the rounded edge 55 (i.e., from side end 45 to side floor 47, or from side floor 47 to side end 45).

In addition, movement of the lever 40 causes the cam 48 to be drawn towards the lever 40 against the force of the latch-spring mechanism 102 as the lever 40 moves from the unsecured vertical position to the secured position. Such a latch assembly 38 may be characterized as an over center draw latch because its spring-biased lever-actuated operation creates over-center action that incorporates natural tension right into the latch-spring mechanism 102 (e.g., a helical spring), which is disposed to act on washer 104 disposed on shaft 42, to prevent accidental opening of the lever 40 when it is in the secured position. A nut 105 or other suitable fastener may be used to secure the washer 104 against the latch-spring mechanism 102.

In accordance with another apparatus embodiment of this disclosure, such as shown by FIGS. 14, 15, 16A, 16B, 16C and 16D, a coupler 72 is provided that can be mounted on platform 14 and that can couple with the recess 23 of a piece of equipment, such as pump 22. Coupler 72 is similar to coupler 12 except that coupler 72 includes a locking mechanism 76, which employs a latch assembly 38 that is attached to a latch bar 108 via shaft 42 extending through hole 110 of the latch bar 108. A retaining clip 112 and nut 113 secures the latch bar 108 on the shaft 42 so that the latch bar 108 is pivotable about axis 44 of the shaft 42. A nut 116 or other suitable fastener secures the washer 104 against latch-spring mechanism 102.

Figure 16A:
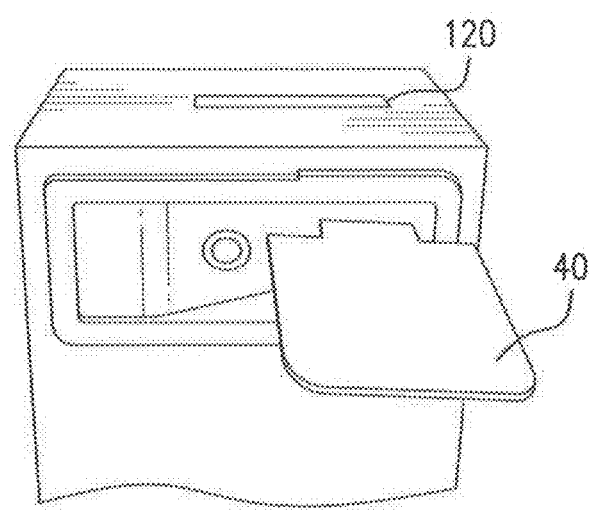
Figure 16B:
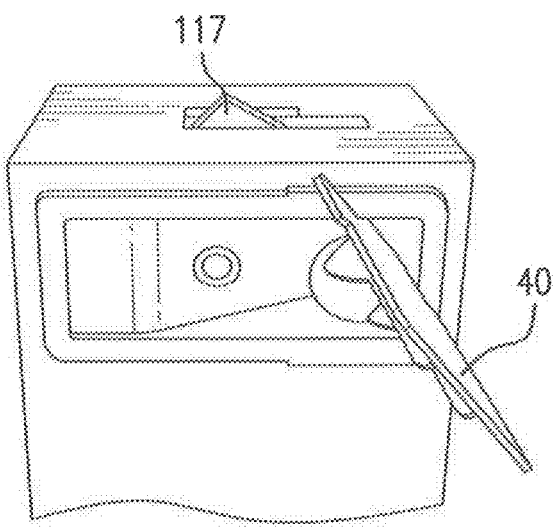
Figure 16C:
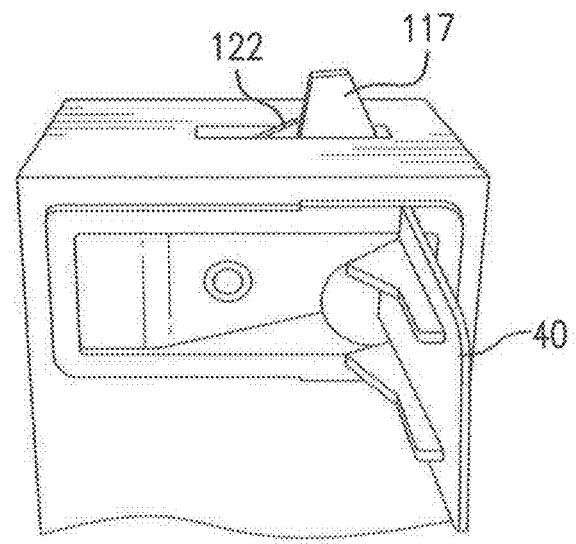
Figure 16D:
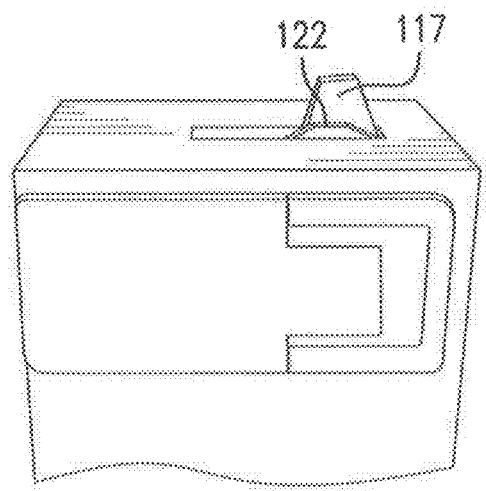

As evident from FIGS. 16A, 16B, 16C and 16D, the latch bar 108 may have a flat profile, and is provided with a tapered end 117 that can be moved from a maximally retracted position (FIG. 16A) that is completely within housing 25 to a maximally extended position (FIG. 16C) by operating the latch assembly 38. More specifically, the locking mechanism 76, which includes latch assembly 38, is moveable with respect to the coupler 72 so as to transition the locking mechanism 76 between its locked configuration, as shown in FIGS. 14 and 16D, and its unlocked configuration, as shown in FIG. 16A, and vice versa. The latch assembly 38 includes a lever 40 that is mounted to cause rotation of shaft 42 when the lever 40 is rotated with respect to the rotational axis 44 of the shaft 42 as evident front FIG. 15. The lever 40 can be transitioned between a secured vertical position, at which rotation about the axis 44 of the shaft 42 is not possible, e.g., as illustrated in FIG. 16D, and an unsecured vertical position in which rotation about the axis 44 of the shaft 42 is possible, e.g., as illustrated in FIG. 16C. Movement of the lever 40 from the unsecured vertical position (FIG. 16C) to an unsecured horizontal position (FIG. 16A) by rotation or pivoting causes the latch bar 108 to move from a maximally extended position (FIGS. 14 and 16C) to a maximally retracted position (FIG. 16A). The latch bar 108, when in the maximally extended position (FIGS. 14 and 16C), can lock the pump 22 to the coupler 72 by engaging a stop 126 formed as part of the housing 35 of the pump 22 when the coupler 72 is properly positioned in the recess 23 of the pump housing 35.

In accordance with an embodiment of this disclosure, a latch bar guide assembly 118 may be provided and attached to the housing 25 of the coupler 72. The latch bar guide assembly 118 is provided with a linear, rectangular orifice 120 formed therein and through which the latch bar tip 117 may extend and retract via rotation or pivoting, as shown by FIGS. 16A, 16B and 16C. Furthermore, the latch bar guide assembly 118 may be provided with a rubber material seal 122 provided by strips of natural or synthetic rubber material, or other suitable sealing material, that seals around the latch bar 108 in a manner that inhibits the penetration of liquid, debris, and mixtures of liquid and debris, through the orifice 120, which tends to minimize contamination of the interior of the coupler 72 with fluids (including bodily fluids), debris and mixtures of fluids and debris. The rubber material seal 122 is a device disposed to wipe the surface of the latch bar tip 117 as the latch bar tip 117 moves through the seal 122.

Unlike the latch pin 46 of the coupler 12, the latch bar 108 of the coupler 72 is not substantially stabilized by the latch bar guide assembly 118. On the contrary, while the latch bar 108 can be rotated or pivoted so it moves to extend and retract through the orifice 120, the latch bar 108 is also free to move in the width direction of the orifice 120. This movement of the latch bar 108 in the width direction of the orifice 120 is due to the cam surface of the lever 40, as discussed above, which causes the shaft 42 to be drawn towards the lever 40 against the force of the latch-spring mechanism 102 as the lever 40 moves from the unsecured vertical position (FIG. 16C) to the secured position (FIG. 16D). In other words, because the latch assembly 38 is an over center draw latch, its spring-biased lever-actuated operation creates over-center action that incorporates natural tension tight into the latch-spring mechanism 102 (e.g., a helical spring), thereby permitting movement of the shaft 42 along the axis 44. Because the shaft 42 is moveable along the axis 44, the latch bar 108 is moveable along the axis 44 because it is secured to the shaft 42.

Consequently, when the lever 40 moves between the unsecured vertical position (FIG. 16C) to the secured vertical position (FIG. 16D), the lever 40 pulls shaft 42 outwardly (i.e., in a direction away from the interior of the housing 25), which pulls the latch bar 108 in the same direction against spring 102. Thus, the lever 40 pulls the latch bar 108 to move within the orifice 120 in a rearward direction (i.e., towards the lever 40 and so as to compress the spring 102 on the shaft 42) so that the latch bar 108 may press against the stop 126 when the coupler 72 is disposed in the recess 23 of the pump housing 35, thereby locking the interfaces 24 and 124 together in a tight manner.

Figure 17A:
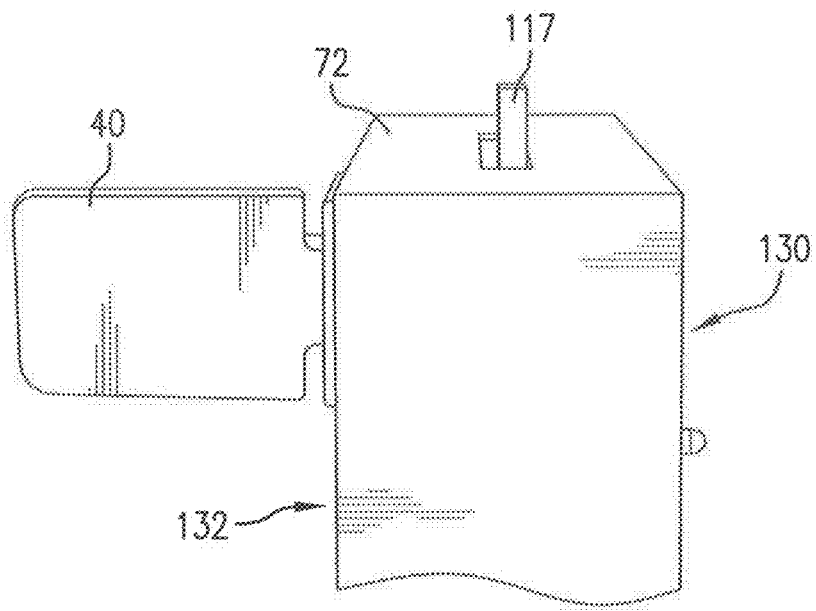
Figure 17B:
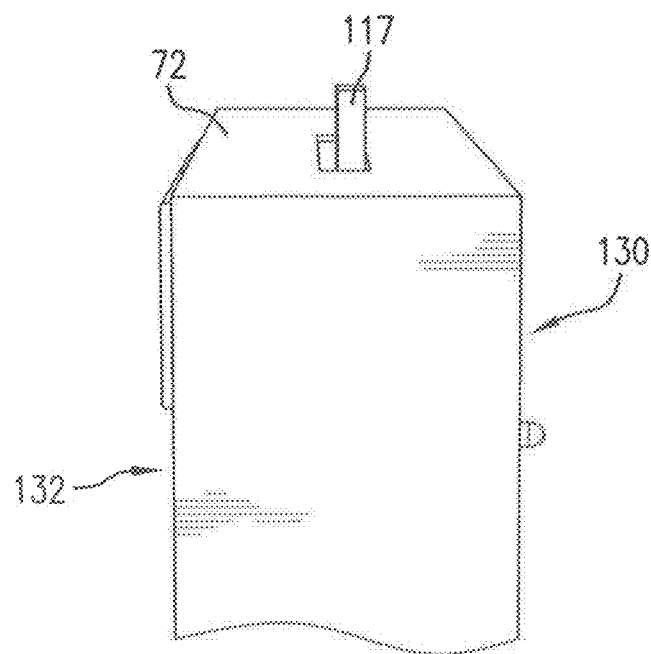

FIGS. 17A and 17B illustrate various positions of the latch bar 108 of the coupler 72 as it moves in the width direction of the orifice 120. FIG. 17A illustrates the forward position of the latch bar 108 when the lever 40 in an unsecured vertical position, and FIG. 17B illustrates the rearward position of the latch bar 108 when die lever 40 is m the secured vertical position. Thus, the latch bar 108 is moveable either towards the front face 130 of the coupler 72, or towards the rear face 132 of the coupler 72, depending upon whether the lever 40 is in the unsecured vertical position or the secured vertical position, respectively.

In accordance with a method embodiment of this disclosure, a method of docking a piece of equipment, such as a peristaltic pump 22, to a heart-lung machine apparatus 10 includes the steps of: (a) disposing a coupler 72 mounted to a platform 14 of a heart-lung machine apparatus 10 into a matingly shaped recess 23 of a housing of the piece of equipment so that the piece of equipment rests on the platform 14, wherein the coupler 12 includes an electrical interface 24 and a locking mechanism 76 that is in an unlocked configuration (b) moving (axially rotating) a lever 40 of the locking mechanism 76 from an unsecured first position (e.g., a substantially horizontal position) to au unsecured second position (e.g., a substantially vertical position) so that a latch bar 108 is moved from a non-latching position (e.g., a maximally retracted position) in which the latch bar 108 does not substantially engage a stop 126 of the housing 35 of the piece of equipment to a latching position (e.g., a maximally extended position) in which the latch bar 108 loosely or lightly engages a stop 126 of the housing of the piece equipment, thereby locking the coupler 72 and the piece of equipment together; and (c) moving (e.g., rotating about a pivot axis formed by a pivot pin 49 attached at one end of the lever) the lever 40 from the unsecured second position to a secured position (e.g., a secured substantially vertical position) in which the lever 40 is substantially flush with an external rim 51 of a well 53 of the locking mechanism 76. These steps am evident from FIGS. 16A to 16D.

Step (a) of this method may include, in accordance with an embodiment, connecting the electrical interface 24 of the coupler 72 to an electrical interface 124 of the piece of equipment 22 so that the piece of equipment is connected to send and/or receive signals from at least one device of the heart-lung machine apparatus 10, or to send and/or receive signals from at least one device of a cardio-pulmonary bypass system that incorporates the heart-lung machine apparatus 10. In accordance with another method embodiment, the lever 40 includes a paddle portion 41 connected to a body portion 43, wherein the body portion 43 has a roughly rectangular shape with a side end 45 separated from a side floor 47 by a rounded edge 55 so that the distance between the pivot pin 49 and the side floor 47 (when the lever 40 is in the secured vertical position) is larger than the distance between the pivot pin 49 and the side end 45 (when the lever 40 is in any of the unsecured positions of FIGS. 16A, 16B and 16C) so that when the lever 40 is pivoted from the unsecured vertical position to the secured vertical position, the surface provided by the side end 45, the rounded edge 55 and the side floor 47 acts as a cam. This cam surface has a shape that effects a snapping transition between the unsecured vertical position and the secured vertical position, and/or vice versa, as resistance to movement gives way abruptly once rotation moves past the rounded edge 55 (i.e., from side end 45 to side floor 47, or from side floor 47 to side end 45).

In addition, movement of the lever 40 causes the latch bar 108 to be drawn towards the lever 40 against the force of the latch-spring mechanism 102 as the lever 40 moves from the unsecured vertical position to the secured vertical position. Such a latch assembly 38 may be characterized as an over center draw latch because its spring-biased lever-actuated operation creates over-center action that incorporates natural tension right into the latch-spring mechanism 102 (e.g., a helical spring), which is disposed to act on washer 104 disposed on shaft 42, to prevent accidental opening of the lever 40 when it is in the secured position. A nut 105 or other suitable fastener may be used to secure the washer 104 against the latch-spring mechanism 102.

Step (c) of this method may further include moving the latch bar 108 from, a forward position to a rearward position within an orifice or slot 120 of the housing 25 of the coupler 22 so that a tip 117 of the latch bar 108 exerts increased pressure against the stop 126 of the piece of equipment 22 when the lever 40 moves from the unsecured vertical position to the secured vertical position. In this way, the tightness of die coupling between the interfaces 24 and 124 may be increased, which ensures more reliable electrical connections between the interlaces 24 and 124.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments failing within the scope of the claims. Also, in the drawings and the description, there have been disclosed exemplary embodiments of the invention and, although specific terms may have been employed, they am unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. An extracorporeal heart-lung support machine apparatus comprising a platform capable of supporting one or more pieces of equipment and at least one coupler mounted to the platform so as to provide a docking interface for a piece of equipment, wherein the coupler comprises:
   an electrical interface configured to matingly engage with a complementarily configured electrical interface of the at least one piece of equipment; and
   a locking mechanism configured to selectively transition between a locked configuration in which a latch member of the locking mechanism is positioned to secure the at least one piece of equipment to the coupler and an unlocked configuration in which the latch member of the locking mechanism is positioned to permit both engagement or disengagement of the electrical interface of the coupler with the electrical interface of the at least one piece of equipment, wherein the locking mechanism includes a latch assembly that is connected to move the latch member linearly between a retracted position and an extended position, wherein in the extended position the latch member is capable of engaging a stop of the at least one piece of equipment.

2. An extracorporeal heart-lung support machine apparatus as recited by claim 1, wherein the at least one piece of equipment is a cardiac pump.

3. An extracorporeal heart-lung support machine apparatus as recited by claim 1, wherein the platform comprises at least one rail arranged with respect to the at least one coupler so that a track disposed on a bottom surface of the at least one piece of equipment is engageable with the at least one rail so as to slide on the at least one rail.

4. An extracorporeal heart-lung support machine apparatus as recited by claim 1, wherein the latch assembly comprises a lever attached by a pivot pin to one end of a shaft so that the lever pivots with respect to the shaft and so that rotation of the lever about an axis of the shaft rotates the shaft about the axis.

5. An extracorporeal heart-lung support machine apparatus as recited by claim 4, wherein a spring is disposed on the shaft so as to exert a force on the lever via the shaft.

6. An extracorporeal heart-lung support machine apparatus as recited by claim 5, wherein the lever is moveable from a substantially horizontal unsecured position to a substantially vertical unsecured position, and from the substantially vertical unsecured position to a substantially vertical secured position.

7. An extracorporeal heart-lung support machine apparatus as recited by claim 6, wherein the lever comprises a body portion that has a roughly rectangular shape with a side end separated from a side floor by a rounded edge so as to provide a cam surface, wherein the cam surface provides a fulcrum so force exerted on the lever compresses the spring when the lever moves from the unsecured vertical position to the secured vertical position.

8. An extracorporeal heart-lung support machine apparatus as recited by claim 7, wherein rotation of the lever about the axis of the shaft is constrained to a quarter turn that moves the lever from the substantially horizontal unsecured position to the substantially vertical unsecured position.

9. An extracorporeal heart-lung support machine apparatus as recited by claim 8, wherein pivoting the lever about 90 degrees about the pivot pin moves the lever from the substantially vertical unsecured position to the substantially vertical secured position.

10. An extracorporeal heart-lung support machine apparatus as recited by claim 9, wherein the lever further comprises a paddle attached to the body portion.

11. An extracorporeal heart-lung support machine apparatus as recited by claim 10, wherein when the lever is in the substantially vertical secured position, the paddle is substantially flush with a rim of a well of the locking mechanism.

12. An extracorporeal heart-lung support machine apparatus as recited by claim 4, wherein the latch member comprises a latch pin, and a cam connects the latch pin to the shaft so that rotation of the lever from the substantially horizontal unsecured position to the substantially vertical unsecured position causes the latch pin to move to the extended position through a latch pin guide device.

13. An extracorporeal heart-lung support machine apparatus as recited by claim 12, wherein when the lever moves from the substantially vertical unsecured position to the substantially vertical secured position, the cam moves toward the lever and the spring is compressed on the shaft.

14. An extracorporeal heart-lung support machine apparatus as recited by claim 13, wherein the latch pin guide device includes a seal member that provides a seal between the latch pin guide device and the latch pin.

15. An extracorporeal heart-lung support machine apparatus as recited by claim 4, wherein the latch member comprises a latch bar having a flat profile.

16. An extracorporeal heart-lung support machine apparatus as recited by claim 15, wherein the latch bar is connected so as to rotate with the shaft so that rotation of the lever from the substantially horizontal unsecured position to the substantially vertical unsecured position causes the latch bar to move to the extended position through a linear orifice formed in a housing of the coupler.

17. An extracorporeal heart-lung support machine apparatus as recited by claim 16, further comprising a seal device disposed to provide a seal at the linear orifice that is penetrable by the latch bar when the latch bar moves from the retracted position to the extended position.

18. A method of docking a peristaltic pump to a heart-lung machine apparatus, wherein the method includes the steps of:
   disposing a coupler mounted to a platform of a heart-lung machine apparatus into a matingly shaped recess of a housing of the pump so that the pump rests on the platform, wherein the coupler includes an electrical interface and a locking mechanism that is in an unlocked configuration;
   axially rotating a lever of the locking mechanism from an unsecured first position to an unsecured second position so that a latch pin is moved from a non-latching position in which the latch pin does not substantially engage a stop of the housing of the pump to a latching position in which the latch pin substantially engages a stop of the housing of the pump, thereby locking the coupler and the pump together; and moving the lever from the unsecured second position to a secured position in which the lever is substantially flush with an external rim of a well of the locking mechanism.

19. A method of docking a peristaltic pump to a heart-lung machine apparatus, wherein the method includes the steps of:

disposing a coupler mounted to a platform of a heart-lung machine apparatus into a matingly shaped recess of a housing of the pump so that the pump rests on the platform, wherein the coupler includes a housing, an electrical interface, and a locking mechanism that is in an unlocked configuration, wherein the electrical interface and the locking mechanism are disposed at least partially within the housing of the coupler;

axially rotating a lever of the locking mechanism from an unsecured first position to an unsecured second position so that a latch bar is moved from a non-latching position in which the latch bar does not substantially engage a stop of the housing of the pump to a latching position in which the latch bar loosely or lightly engages a stop of the housing of the pump, thereby locking the coupler and the pump together;

moving the lever from the unsecured second position to a secured position in which the lever is substantially flush with an external rim of a well of the locking mechanism; and moving the latch bar from a forward position to a rearward position within a linear orifice of the housing of the coupler so that a tip of the latch bar exerts increased pressure against the stop of the pump when the lever moves from the unsecured second position to the secured position.

20. An extracorporeal heart-lung support machine apparatus comprising a planar platform capable of supporting multiple pieces of equipment and a plurality of couplers mounted to the planar platform so as to provide a docking interface for each one of the multiple pieces of equipment, wherein each coupler comprises:

an electrical interface configured to matingly engage with a complementarily configured electrical interface of the at least one of the multiple pieces of equipment; and a locking mechanism configured to selectively transition between a locked configuration in which a latch member of the locking mechanism is positioned to secure the at least one of the multiple pieces of equipment to the coupler and an unlocked configuration in which the latch member of the locking mechanism is positioned to permit both engagement or disengagement of the electrical interface of the coupler with the electrical interface of the at least one of the multiple pieces of equipment.

21. An extracorporeal heart-lung support machine apparatus as recited by claim 20, wherein the at least one of the multiple pieces of equipment is a cardiac pump.

22. An extracorporeal heart-lung support machine apparatus as recited by claim 20, wherein the planar platform comprises at least one rail arranged with respect to each coupler so that a track disposed on a bottom surface of each piece of equipment is engageable with the at least one rail so as to slide on the at least one rail.

* * * * *